United States Patent
Wall

(10) Patent No.: US 6,935,177 B2
(45) Date of Patent: Aug. 30, 2005

(54) METHOD FOR AN ENTROPY FILTER ECHO PROCESSING IN TIME-OF-FLIGHT OR LEVEL MEASUREMENT SYSTEMS

(75) Inventor: Graham D. Wall, Peterborough (CA)

(73) Assignee: Siemens Milltronics Process Instruments Inc., Peterborough (CA)

( * ) Notice: Subject to any disclaimer, the term of this patent is extended or adjusted under 35 U.S.C. 154(b) by 17 days.

(21) Appl. No.: 10/674,846

(22) Filed: Sep. 29, 2003

(65) Prior Publication Data

US 2005/0066731 A1 Mar. 31, 2005

(51) Int. Cl.⁷ .......................... G01N 29/04; G01S 15/00
(52) U.S. Cl. .......................... 73/597; 73/598; 73/602; 367/100
(58) Field of Search .................. 73/597, 598, 600, 73/602, 290; 367/87, 100, 101, 908, 135, 102, 99

(56) References Cited

U.S. PATENT DOCUMENTS

| | | | | |
|---|---|---|---|---|
| 5,508,974 A | * | 4/1996 | Meyer et al. | 367/99 |
| 5,587,969 A | * | 12/1996 | Kroemer et al. | 367/99 |
| 5,996,407 A | * | 12/1999 | Hewitt | 73/290 V |
| 6,046,960 A | * | 4/2000 | Kumar | 367/87 |
| 6,545,946 B1 | * | 4/2003 | Huss et al. | 367/99 |

OTHER PUBLICATIONS

U.S. Appl. No. 10/674,614, filed Sep. 30, 2003, Adam Lomas.
U.S. Appl. No. 10/675,331, filed Sep. 30, 2003, Marian Jozef Walter Slezak.
U.S. Appl. No. 10/672,582, filed Sep. 25, 2003, Frank Daigle.
U.S. Appl. No. 10/683,198, filed Oct. 10, 2003, Quinton Lyon.

* cited by examiner

Primary Examiner—Hezron Williams
Assistant Examiner—Jacques M. Saint-Surin
(74) Attorney, Agent, or Firm—Workman Nydegger

(57) ABSTRACT

A method for processing echoes in a time-of-flight ranging system or level measurement system. The method comprises applying an entropy filter to the echo profile. The entropy filter comprises determining the information content in the echo profile. The entropy filter determines the occurrences of a pattern in the bit stream representing magnitudes in the echo profile. Repeated occurrences of the pattern are used to characterize the echo signal as having low randomness (i.e. higher information content) indicative of a potential echo pulse or as having high randomness (i.e. lower information content) indicative of noise.

21 Claims, 3 Drawing Sheets

METHOD FOR AN ENTROPY FILTER ECHO PROCESSING IN TIME-OF-FLIGHT OR LEVEL MEASUREMENT SYSTEMS

FIELD OF THE INVENTION

The present invention relates to signal processing, and more particularly to a method for an entropy filter for echo processing in level measurement or time of flight ranging systems.

BACKGROUND OF THE INVENTION

Pulse-echo acoustic ranging systems, also known as time-of-flight ranging systems, are commonly used in level measurement applications. Pulse-echo acoustic ranging systems determine the distance to a reflector (i.e. reflective surface) by measuring how long after transmission of a burst of energy pulses the echoes or reflected pulses are received. Such systems typically use ultrasonic pulses, pulsed radar or microwave signals.

Pulse-echo acoustic ranging systems generally include a transducer and a signal processor. The transducer serves the dual role of transmitting the energy pulses and receiving the reflected energy pulses or echoes. An echo profile is generated from the received energy pulses. Echo pulses are identified in the echo profile by the signal processor, and the distance or range of the object is calculated based on the transmit times of the transmitted energy pulses and the receive echo pulses.

To provide accurate level measurements, the echo pulses must be precisely detected and processed. One approach involves transmitting multiple transmit pulses, i.e. "shots", and averaging the echo positions associated with the multiple transmit pulses. For noisy environments, for example, a waste water tank, the number of shots is increased for the average in an effort to reduce the effects of noise. The aim of this approach is to dampen or smooth random deviations in the echo pulse position in an echo profile. However, the technique does not prevent noisy profiles from becoming part of the average. In a noisy environment, such as filling a waste water tank, the level measurements can be very imprecise because the average echo-position is based on a large number noisy echoes.

The commonly used technique for finding echoes in an echo profile involves generating a time varying threshold or TVT curve. The TVT curve provides a baseline or line on the echo profile which is above the noise level in the echo profile. Valid echoes appear above the TVT curve. Various algorithms and techniques are known in the art for determining the noise floor and generating the TVT curve.

Two solutions for improving level measurements for echo-based systems in the presence of noise comprise; (1) increasing the number of shots taken and averaging the results; and (2) measuring the noise floor and using the average noise level to generate a TVT curve to assist in the interpretation of the echo profile curve.

A typical echo profile indicated by reference 100 is shown in FIG. 1 together with a TVT curve indicated by reference 120. The first portion of the echo profile 100 comprises a half pulse 140 which corresponds to the ring-down in the transducer. The ring-down compris s the period or interval in which the transducer is still "ringing down" from the transmit pulses emitted and as such this interval is not considered for detecting reflected energy pulses. Following the ring-down 140, the echo profile 100 comprises a number of pulses 160, indicated individually as 160a, 160b, 160c, 160d and 160e, in FIG. 1. Using the TVT curve 120, the pulses 160a, 160b, 160c and 160d are identified as valid receive echo pulses. The portion of the echo profile 100 that falls below by the TVT curve 120 is considered to be noise and in FIG. 1 is indicated generally by reference 150. For instance, the last pulse 160e falls below the TVT curve 120 and is considered to comprise noise.

While the TVT technique has been used successfully in level measurement and time-of-flight ranging systems, there are shortcomings. First, generating the noise floor and the TVT curve can be a processor intensive process. Secondly, most TVT curves require manual adjustments to provide the best performance, and thirdly different TVT curves will work better in some situations rather than others.

Accordingly, there remains a need to provide a system and techniques which improve the processing of the reflected energy pulses or echoes.

BRIEF SUMMARY OF THE INVENTION

The present invention provides a method for an entropy-based filter for an echo processing in a time-of-flight or a level measurement system. According to one aspect, the entropy filter is applied to process or filter echo profiles that do not have a minimum amount of bit-wise information, i. . . a low degree of randomness.

In a first aspect, the present invention provides a method for generating an echo signal in a time-of-flight ranging system, the method comprises the steps of: transmitting one or more bursts of energy towards a reflective surface; receiving reflected pulses from the reflective surface, and converting the reflected pulses into an echo signal, the echo signal includes one or more potential echo pulses; applying an entropy filter to the echo signal, the entropy filter includes determining whether information contained in the echo signal corresponds to a valid echo pulse or is substantially noise; distinguishing those of the echo pulses determined as comprising noise in the echo signal.

In another aspect, the present invention provides a level measurement device for measuring a distance to a material having a surface, the level measurement device comprises: a transducer for emitting energy pulses and detecting energy pulses reflected by the surface of the material; a controller having a receiver and a transmitter; the transducer includes an input port operatively coupled to the transmitter and is responsive to the transmitter for emitting the energy pulses, and the transducer includes an output port operatively coupled to the receiver for outputting reflected energy pulses coupled by the transducer: the receiver includes a converter for converting the reflected energy pulses into signals; the controller includes a program component for generating an echo profile based on the signals; the controller includes another program component for applying an entropy based filter to the echo profile.

In a yet further aspect, the present invention provides a time of flight ranging system comprising: a transducer for emitting energy puls s and detecting reflected energy pulses; a controller having a receiver and a transmitter; the transducer includes an input port operatively coupled to the transmitter and is responsive to the transmitter for emitting the energy pulses, and the transducer includes an output port operatively coupled to the receiver for outputting reflected energy pulses coupled by the transducer; the receiver includes a converter for converting the reflected energy pulses into signals; the controller includes a program component for generating an echo profile based on the signals, the echo profile comprises potential echoes and potential noise; the controller includes another program component for applying an entropy filter to the potential echoes to differentiate the potential noise from said potential echoes.

Other aspects and features of the present invention will become apparent to those ordinarily skilled in the art upon review of the following description of specific embodiments of the invention in conjunction with the accompanying drawings.

BRIEF DESCRIPTION OF THE DRAWINGS

Reference is next made to the accompanying drawings which show, by way of example, embodiments of the present invention and in which.

DETAILED DESCRIPTION OF EMBODIMENTS OF THE INVENTION

Figure 1:
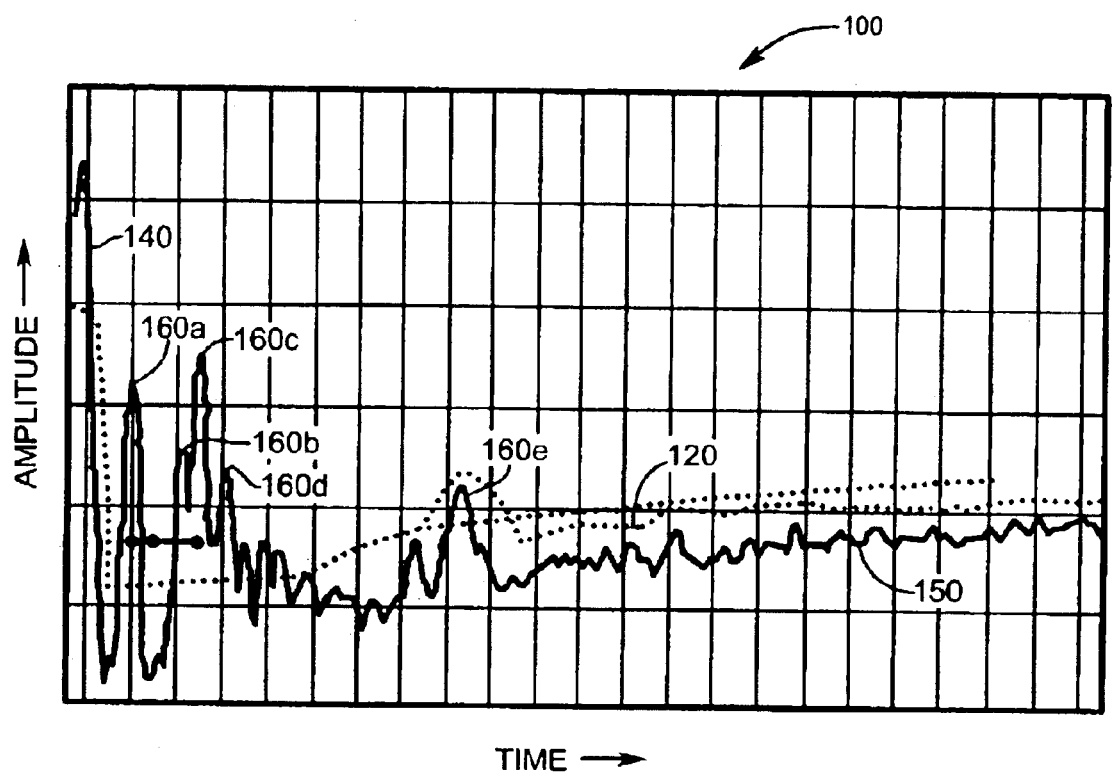
FIG. 1 is a graphic representation of an echo signal waveform, a noise floor level waveform and a noise signal waveform for a time-of-flight ranging system.
Figure 2A:
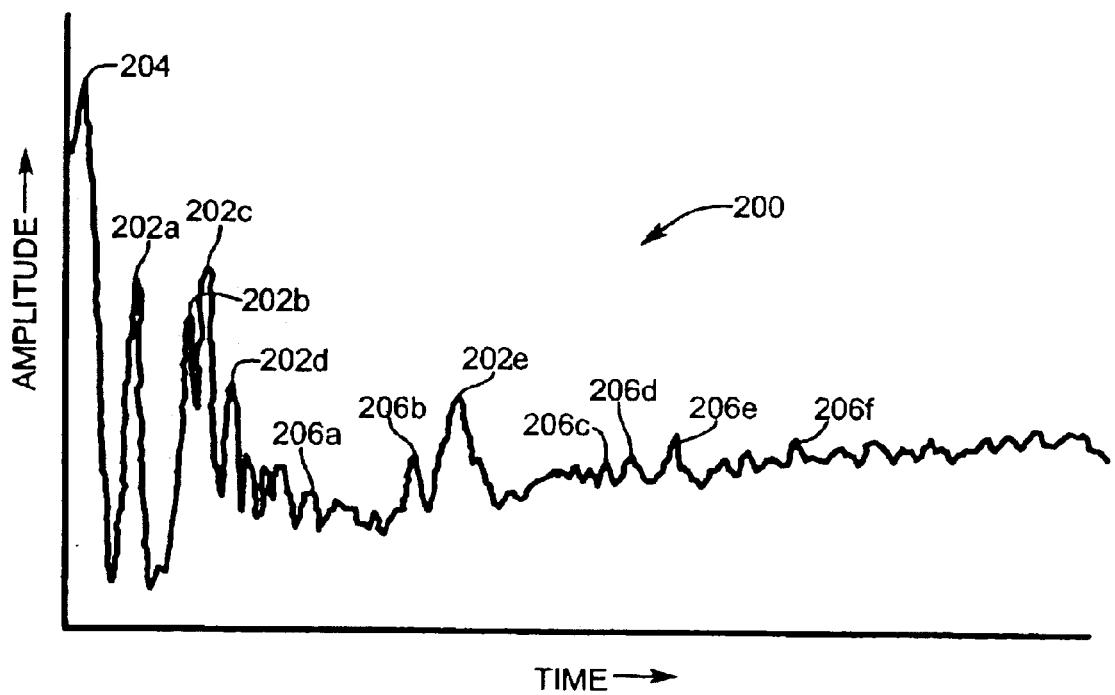
FIG. 2(a) is an echo profile waveform with echo pulses identified in accordance with the present invention.

Reference is first made to FIG. 2(a) which shows an echo profile 200 generated in a time-of-flight ranging or level measurement system and suitable for processing in accordance with the present invention.

The echo profile 200 is generated in the operation of the level measurement device (or the time-of-flight ranging system). In known manner, the level measurement device includes a transducer (e.g. ultrasonic, microwave or radar), a controller or signal processor unit, an analog-to-digital (A/D) converter, a transmitter, a receiver, and a power supply unit. The transducer emits a transmit pulse or energy burst directed at a surface to be measured. The surface reflects the transmit energy burst and the reflected energy pulses are coupled by the transducer and converted into electrical signals. The electrical signals are applied to the receiver and sampled and digitized by the A/D converter. The signal processor, for example a microprocessor operating under firmware control, takes the digitized output and generates the echo profile 200 having a form as shown in FIG. 2. The echo profile 200 is characterized by one or more valid echoes 202, Indicated individually by references 202a, 202b, 202c, . . . The echoes 202 correspond to reflected energy pulses. The echo profile 200 also includes a ring-down portion 204 which corresponds to the 'ringing down' of the transducer after transmission of the energy burst or pulses. It is normally not possible to detect receive echoes during the ring-down Interval. As also shown in FIG. 2(a), the echo profile 200 includes a multitude of pulses or bumps 206, indicated individually by references 206a, 206b, 206c, 206d, 206e, 206f, . . . which are identified as noise. As will be described in more detail, the noise pulses or elements 206 in the echo profile 200 may be distinguished by utilizing the entropy filter in accordance with the invention, or by applying a TVT analysis in conjunction with the entropy filter according to the present invention.

In known manner, the controller unit executes an algorithm (e.g. a process or function implemented in firmware) which uses the echo profile 200 to calculate the range, i.e. the distance to the reflective surface, from the time it takes for the reflected energy pulse to travel from the reflective surface to the transducer. From this calculation, the distance to the surface of the liquid (i.e. the material contained in the vessel) and thereby the level of the liquid is determined. The controller, e.g. microprocessor or microcontroller, is suitably programmed to perform these operations as will be within the understanding of those skilled in the art.

As will now be described in more detail, the subject invention is directed to a method or process for an entropy filter for analyzing an echo profile for echoes or pulses. The method and processing steps as described below may be embodied in the controller as a program component or firmware.

Figure 2B:
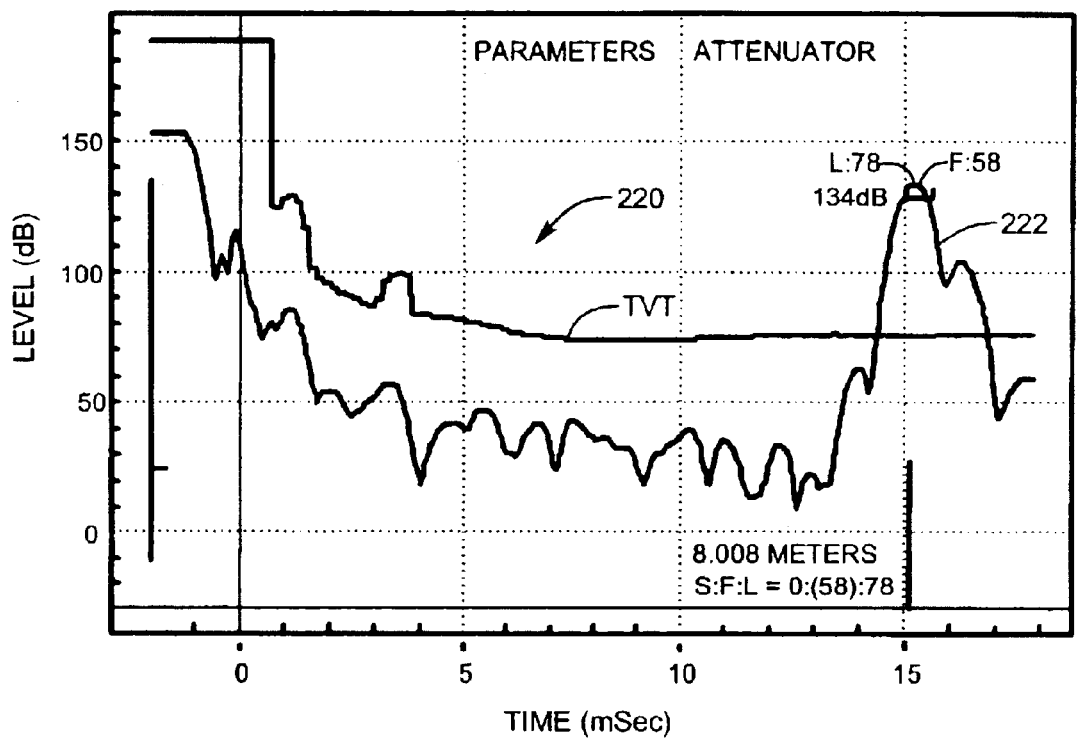
FIG. 2(b) is an exemplary echo profile with a defined or valid echo pulse.
Figure 2C:
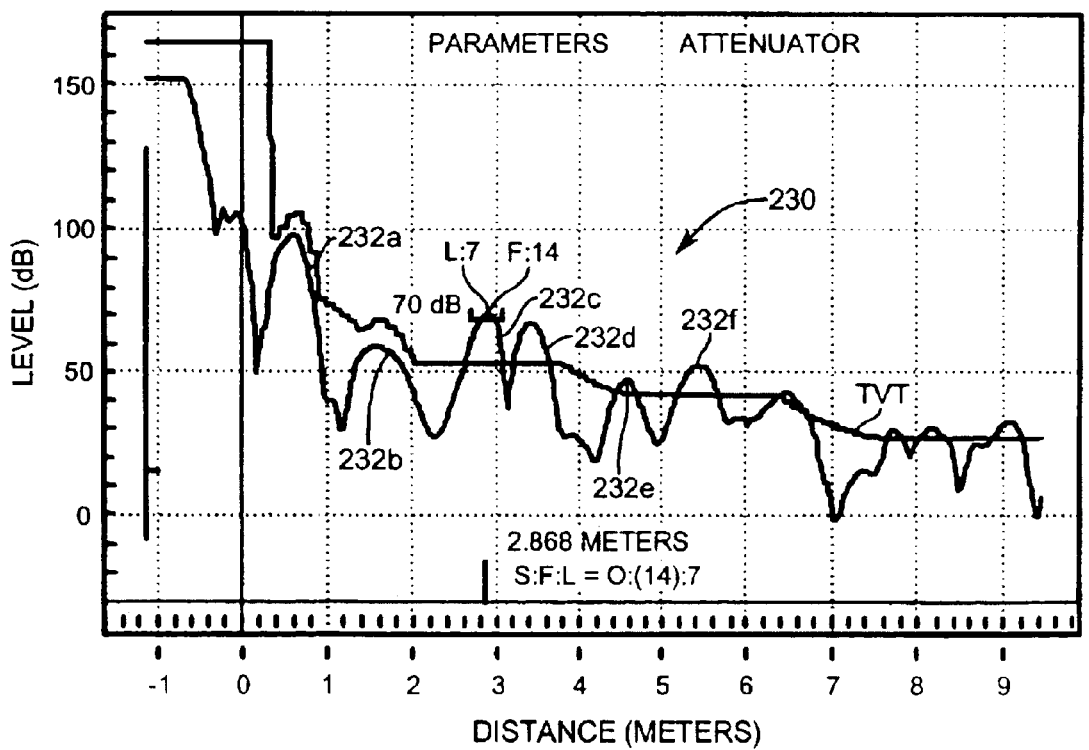
FIG. 2(c) is an exemplary echo profile comprising mostly noise with no clearly defined echo pulse.

In operation the entropy filter distinguishes or rejects echo profiles, or 'shots', that do not contain a minimum threshold amount of information, to define a valid echo pulse, on the basis that the more disordered the bit stream in the echo profile, the less reliable the echoes (i.e. shots) for measurement, regardless of the magnitude or threshold level of the echoes. An exemplary echo profile 220 having a defined echo pulse 222 is depicted in the FIG. 2(b). In FIG. 2(b), a TVT curve 224 is also included on the plot for the echo profile 220. Another exemplary echo profile 230 is depicted in FIG. 2(c). The plot in FIG. 2(c) also includes a TVT curve 234. As compared to the echo profile 220 of FIG. 2(b), the echo profile 230 of FIG. 2(c) is a much more noisier profile with a majority of pulses 232, indicated individually as 232a, 232b, 232c, 232d, 232e and 232f, failing below or around the TVT curve 234, As a result it is very difficult to ascertain a clearly defined echo pulse for the echo profile 230 of FIG. 2(c). According to this aspect of the Invention, application of the entropy filter to the echo profile 230 of FIG. 2(c) determines more random information which manifests itself in irregular contours, e.g. the noise pulses 232. The high degree of randomness is indicative of noise as compared to valid echo pulses. For the echo profile 220 of FIG. 2(b), application of an entropy filter in accordance with the present invention determines higher information content (i.e. a low degree of randomness) and the echo pulse 222 is identifiable.

In accordance with this aspect, the entropy of an echo profile (e.g. the echo profile 220 shown in FIG. 2(b)) is determined by matching a reference set of short bit-patterns with selected portions of the bit-stream comprising the echo profile to provide an information content estimation for the echo profile. The portions of the bit-stream for the echo profile may be randomly selected.

One technique for analyzing a random portion of the echo profile involves applying a Monte Carlo method. Using the Monte Carlo method, if each reference pattern occurs the same number of times in the selected portion, then the selected portion, e.g. echo profile, has the minimum amount of information possible. In addition, the more that some reference patterns appear in the bit-stream, the more information content and therefore less entropy, i.e. randomness the echo profile is estimated to have. This increases the likelihood or probability that the echo profile comprises an accurate or valid echo position.

According to this aspect, the echo profile is provided as a bit-stream comprising a binary sequence represented by X and containing K possible patterns or symbols, where each pattern $x_k$ occurs with probability $p_k$. The entropy of the bit-stream, i.e. echo profile, is defined by a function H(x) as follows in equation (1):

$$H(x) = -\sum_{k=1}^{K} p_k \log_2 p_k \quad (1)$$

If a symbol or pattern occurs with probability 1 for example, the bit-stream for the echo profile comprises 1's, then the entropy is at a minimum, i.e. $H(x)=0$. If there are K possible symbols or patterns, and each of the symbols occurs with equal probability, then the entropy is at a maximum, i.e. $H(x)=\log_2 K$ and the echo profile comprises noise.

For example, for an echo profile X, the entropy is determined by matching 14 symbols, i.e. K=14 comprising short binary patterns, $x_k$, with (e.g. randomly selected) portions of the echo profile. In this example, the short binary patterns, $x_k$, comprise 0, 1, 00, 01, 10, 11, 001, 010, 100, 110, 011, 101, 000, 111. The echo profile X comprises a bit-stream representing echo profile magnitudes which are binned with respect to a radix and precision.

According to another aspect, each echo profile, for example, a plurality of echo profiles generated from a batch of "shots" for a measurement, may be ranked according to its entropy. The rankings may then be used by processes in the application software for the level measurement system to select the most accurate echo positions for determining an average echo position and corresponding level measurement.

Figure 3:
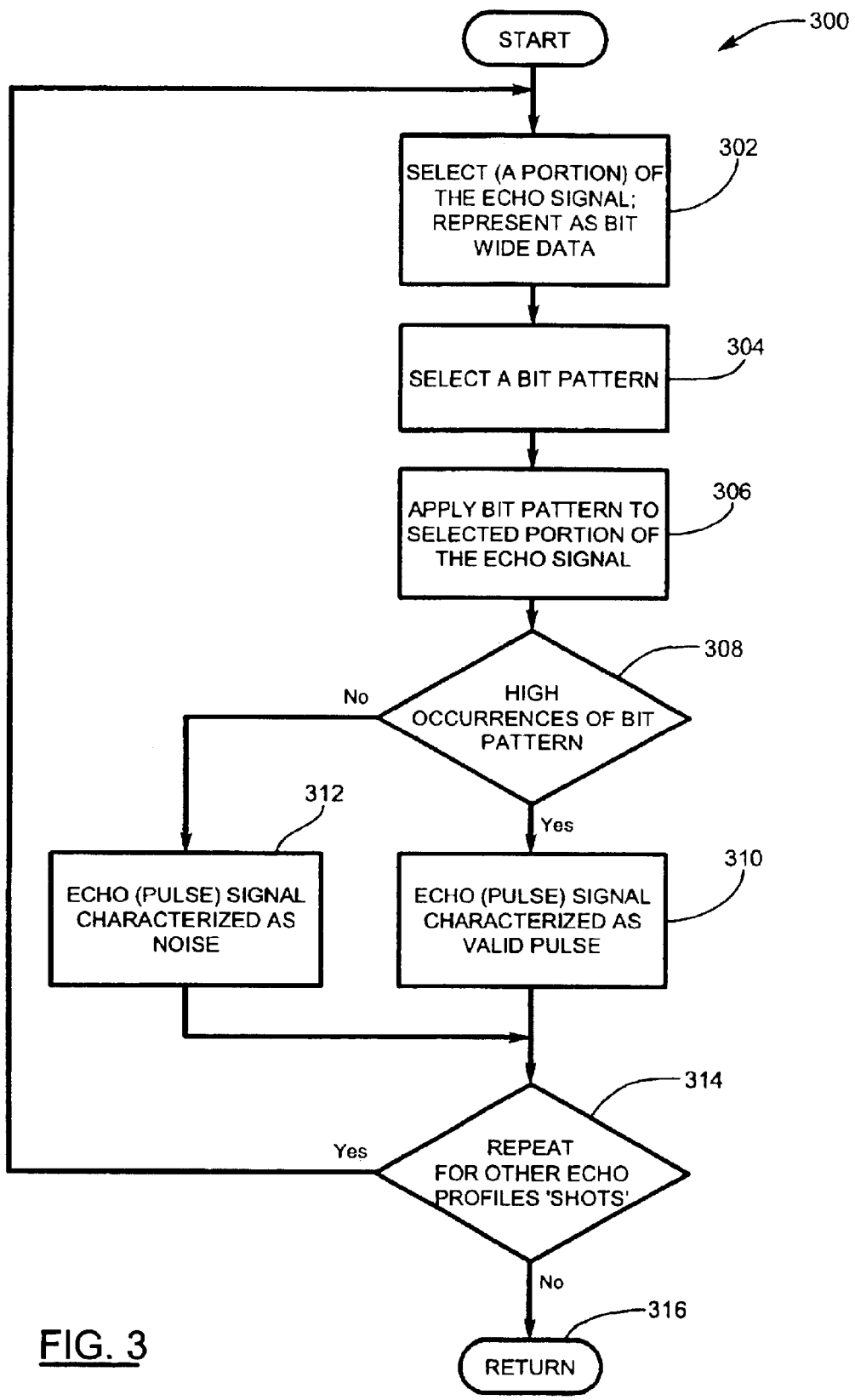
FIG. 3 is a flow chart showing the processing steps for an entropy filter for processing an echo profile in accordance with the present invention.

Reference is next made to FIG. 3 which shows in flowchart form an entropy filter process 300 in accordance with the present invention. As indicated in block 302, the first step in the entropy filter process 300 comprises selecting a portion of the echo profile (in the alternative the complete echo profile may be considered). The selected portion of the echo profile is represented digitally, i.e. as a bit wise data stream, with digital values representative of magnitudes in the echo profile. Next in block 304, one or more bit patterns are selected. The bit patterns may be generated or read from a look-up table stored in memory. Next in block 306, the bit pattern(s) are applied to the bit wise representation of the echo profile, and the number of occurrences of the bit pattern in the echo profile is determined. As described above, the Monte Carlo method or technique may be utilized as described above. The number (or probability) of occurrences of the bit pattern(s) indicates the entropy of the echo profile. A high number of occurrences corresponds to a low entropy and indicates an echo profile with low noise content and therefore a valid echo pulse. A low number of occurrences corresponds to a high entropy which is indicative of noise. Based on the number of occurrences (decision block 308), the echo pulse profile is characterized as an echo profile having a defined echo pulse (block 310) or as noise (block 312). If more than one echo profile is being considered, for example, to generate an average echo profile using application of the entropy filter to a number of echo profiles (i.e. shots), then the process is repeated (decision block 314), otherwise the process returns (step 316) to the calling function or process being executed by the controller. It will be appreciated that the processing steps illustrated in FIG. 3 are exemplary, and as such may be implemented in a different fashion or order.

An exemplary implementation in the c programming language is provided as follows. The specific implementation details of the code will be within the understanding of those skilled in the art.

Pseudo Code
© Siemens Militronics Process Instruments Inc. 2002–2003

```
float calculateShotEntropy(void)
{
/* randomly select a section of profile data */
profileOffset = (size_t)(profileSize * rand( ));
sectionStart = profileOffset;
sectionEnd = profileOffset + sectionSize;
/* convert profile section to binary */
X = convertToBinary(profileData, sectionStart, sectionEnd);
/* calculate entropy for the section */
entropy = 0.0;
for (k = 0; k < numberOfSymbols; k++)
    {
    /* sum number of occurrences of this symbol in section */
    numOccurences = 0;
    for (bitOffset = 0; bitOffset < sectionSizeInBits; bitOffset++)
        {
        if (matches(symbol[k], X[bitOffset])
            {
            numOccurrences++;
            }
        }
    /* probability for this symbol occurring is number of occurrences
    divided by number of possible occurrences */
    p[k] = numOccurrences / (sectionSizeInBits - 1);
    /* Add entropy for this symbol to running total for entropy */
    entropy += -(p[k]*log(p[k],2));
    }
return(entropy);
}
```

It will be appreciated that the entropy shot filter processing in accordance with the present invention complements and/or improves the results from averaging batches of shot data. Averaging is an attempt to smooth out random perturbations in the echo profile, however, in practice averaging tends to only remove noise that has a uniform probability distribution. The entropy filtering technique according to the present invention detects noise with arbitrary probability distributions according to the symmetries of the selected set of reference bit patterns. Furthermore, the entropy filter processing may be utilized to complement existing noise rejection techniques, for example, calculation of a noise floor for generating a TVT.

The present invention may be embodied in other specific forms without departing from the spirit or essential characteristics thereof. Certain adaptations and modifications of the invention will be obvious to those skilled in the art. Therefore, the above discussed embodiments are considered to be illustrative and not restrictive, the scope of the invention being indicated by the appended claims rather than the foregoing description, and all changes which come within the meaning and range of equivalency of the claims are therefore intended to be embraced therein.

What is claimed is:

1. A method for generating an echo signal in a time-of-flight ranging system, said method comprising the steps of:
    transmitting one or more bursts of energy towards a surface;
    receiving reflected pulses from said surface, and converting said reflected pulses into an echo signal, said echo signal including one or more potential echo pulses;
    applying an entropy filter to said echo signal, said entropy filter including determining whether information contained in said echo signal corresponds to a valid echo pulse or is substantially noise;
    distinguishing those of said echo pulses determined as comprising noise in said echo signal.

2. The method as claimed in claim 1, wherein said step of applying an entropy filter comprises determining the number of times a predetermined pattern is found in a potion of said echo signal.

3. The method as claimed in claim 2, wherein said predetermined pattern comprises a bit pattern and said echo signal or a portion of said echo signal is characterized as a bit stream representing magnitude values in said echo signal.

4. The method as claimed in claim 3, wherein said predetermined pattern is applied according to a Monte Carlo technique.

5. The method as claimed in claim 1, comprising the steps of generating a plurality of echo signals, and applying said entropy filler to each of said entropy signals to generate to an entropy level for each of said entropy signals, and ranking said echo signals based on said entropy levels.

6. The method as claimed in claim 5, wherein said echo signals having entropy levels indicated low randomness are averaged to generate an average echo signal.

7. The method as claimed in claim 5, wherein said step of applying an entropy filter comprises determining the number of times a predetermined pattern is found in a portion of said echo signal.

8. The method as claimed in claim 7, wherein said predetermined pattern comprises one or more bit patterns and the portion of said echo signal is characterized as a bit stream representing magnitude values in said echo signal.

9. The method as claimed in claim 8, wherein said bit patterns are applied according to a Monte Carlo technique.

10. The method as claimed in claim 1, wherein said step of applying an entropy filter comprises selecting a portion of said echo signal and comparing said selected portion to a predetermined pattern, and if said selected portion matches said predetermined pattern within a threshold level, said echo signal is identified as comprising an echo pulse.

11. The method as claimed in claim 10, wherein said selected portion comprises a bit stream corresponding to magnitude values in said echo signal.

12. The method as claimed in claim 11, wherein said predetermined pattern comprises a bit pattern.

13. A level measurement device for measuring a distance to a material having a surface, said level measurement device comprising:

a transducer for emitting energy pulses and detecting energy pulses reflected by the surface of the material;

a controller having a receiver and a transmitter;

said transducer having an input port operatively coupled to said transmitter and being responsive to said transmitter for emitting said energy pulses, and said transducer including an output port operatively coupled to said receiver for outputting reflected energy pulses coupled by the transducer;

said receiver including a converter for converting said reflected energy pulses into signals;

said controller including a program component for generating an echo profile based on said signals;

said controller including another program component for applying an entropy based filter to the echo profile.

14. The device as claimed in claim 13, wherein said program component for applying an entropy-based filter comprises a program component for determining the information content in a portion of said echo profile.

15. The device as claimed in claim 14, wherein a high information content is indicative of a valid echo in said echo profile, and wherein a low information content is indicative of noise in said echo profile.

16. The device as claimed in claim 14, wherein said program component for determining the information content comprises a component for determining occurrences of one or more pre-selected patterns in the portion of said echo profile.

17. The device as claimed in claim 16, wherein said pre-selected pattern comprises a bit pattern and said portion of said echo profile is characterized as a bit stream representing magnitude values in said echo profile.

18. The device as claimed in claim 17, wherein said pre-selected pattern is applied according to a Monte Carlo technique.

19. A time of flight ranging system comprising:

a transducer for emitting energy pulses and detecting reflected energy pulses;

a controller having a receiver and a transmitter;

said transducer having an input port operatively coupled to said transmitter and being responsive to said transmitter for emitting said energy pulses, and said transducer including an output port operatively coupled to said receiver for outputting reflected energy pulses coupled by the transducer;

said receiver including a converter for converting said reflected energy pulses into signals;

said controller including a program component for generating an echo profile based on said signals, maid echo profile comprising potential echoes and potential noise; and said controller including another program component for applying an entropy filter to said echo profile to differentiate said potential noise from said potential echoes.

20. The device as claimed in claim 19, wherein said program component for applying an entropy-based filter comprises a program component for determining the information content in a portion of said echo profile.

21. The device as claimed in claim 20, wherein a high information content is indicative of a valid echo in said echo profile, and wherein a low information content is indicative of noise in said echo profile.

* * * * *